US009364187B2

(12) United States Patent
Lacey

(10) Patent No.: US 9,364,187 B2
(45) Date of Patent: Jun. 14, 2016

(54) PACKAGING DESIGN FOR CT DETECTOR

(71) Applicant: General Electric Company, Schenectady, NY (US)

(72) Inventor: Joseph Lacey, Cambridge, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/269,087

(22) Filed: May 3, 2014

(65) Prior Publication Data

US 2015/0319830 A1   Nov. 5, 2015

(51) Int. Cl.
*A61B 6/00* (2006.01)
*H01L 27/146* (2006.01)
*G01T 1/24* (2006.01)

(52) U.S. Cl.
CPC ............. *A61B 6/4266* (2013.01); *A61B 6/4411* (2013.01); *G01T 1/243* (2013.01); *G01T 1/244* (2013.01); *H01L 27/14601* (2013.01); *A61B 6/4208* (2013.01); *A61B 6/4488* (2013.01); *H01L 27/146* (2013.01)

(58) Field of Classification Search
CPC .......... A61B 6/00; A61B 6/42; A61B 6/4208; A61B 6/4266; A61B 6/44; A61B 6/4411; A61B 6/4488; G01T 1/00; G01T 1/02; G01T 1/16; G01T 1/24; G01T 1/243; G01T 1/244; H04N 1/00519; H04N 1/00522; H04N 1/00525; H04N 1/00537; H04N 1/00551; H04N 1/00554; H04N 1/00557; H04N 1/00559; H01L 23/34; H01L 23/367; H01L 23/3672; H01L 23/3675; H01L 25/00; H01L 25/03; H01L 25/04; H01L 25/042; H01L 25/065; H01L 25/0655; H01L 25/10; H01L 25/105; H01L 25/18; H01L 25/50; H01L 27/00; H01L 27/10; H01L 27/12; H01L 27/14; H01L 27/142; H01L 27/144; H01L 27/146; H01L 27/14601; H01L 27/1465
USPC ............... 378/19, 189, 204, 210; 250/370.01, 250/370.08, 370.09, 370.15, 371, 238, 239, 250/428–430, 435, 437, 443.1, 526
See application file for complete search history.

(56) References Cited

U.S. PATENT DOCUMENTS

| | | | | |
|---|---|---|---|---|
| 6,236,051 | B1 * | 5/2001 | Yamakawa et al. | 250/370.1 |
| 6,448,544 | B1 * | 9/2002 | Stanton et al. | 250/208.1 |
| 7,849,516 | B2 * | 12/2010 | Binnig et al. | 850/62 |

(Continued)

FOREIGN PATENT DOCUMENTS

KR   1020130133688 A   12/2013

OTHER PUBLICATIONS

International Search Report from corresponding PCT application No. PCT/US2015/027962; 3 pages.

*Primary Examiner* — Anastasia Midkiff
(74) *Attorney, Agent, or Firm* — Fletcher Yoder, P.C.

(57) ABSTRACT

A CT system includes a gantry having an opening for receiving an object to be scanned, an x-ray tube attached to the gantry, and a detector assembly. The detector assembly is positioned to receive x-rays that pass through the object and includes a light-sealed enclosure formed by at least first and second rails, a back support, and a light seal structure, and a plurality of liquid-cooled modules positioned in the enclosure. Each module includes a digital cable that passes from inside the enclosure, and each module is configured to convert the x-rays to a digital signal and output the signal via a digital cable.

17 Claims, 8 Drawing Sheets

(56) References Cited

U.S. PATENT DOCUMENTS

| | | | |
|---|---|---|---|
| 2003/0146390 A1* | 8/2003 | Vafi et al. | 250/370.15 |
| 2005/0117698 A1* | 6/2005 | Lacey et al. | 378/19 |
| 2007/0278412 A1* | 12/2007 | Hackenschmied et al. | 250/363.08 |
| 2011/0129069 A1 | 6/2011 | Freund | |
| 2011/0291017 A1* | 12/2011 | Frach | 250/366 |
| 2012/0183119 A1* | 7/2012 | Ikhlef et al. | 378/19 |
| 2013/0037251 A1 | 2/2013 | Joshi et al. | |
| 2013/0039458 A1 | 2/2013 | Ikhlef et al. | |
| 2013/0108019 A1 | 5/2013 | Tkaczyk et al. | |
| 2013/0134313 A1* | 5/2013 | Niederlohner et al. | 250/363.03 |
| 2013/0279648 A1 | 10/2013 | Joshi et al. | |
| 2013/0284936 A1* | 10/2013 | McBroom et al. | 250/363.03 |
| 2013/0322603 A1 | 12/2013 | Kurochi et al. | |
| 2013/0343507 A1* | 12/2013 | Gregerson et al. | 378/4 |

\* cited by examiner

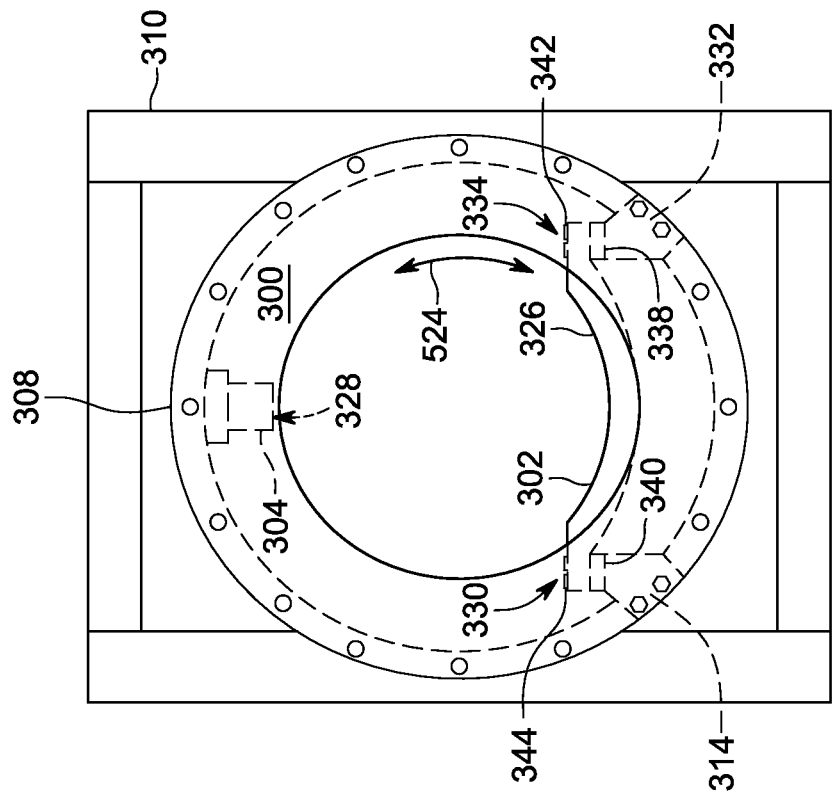
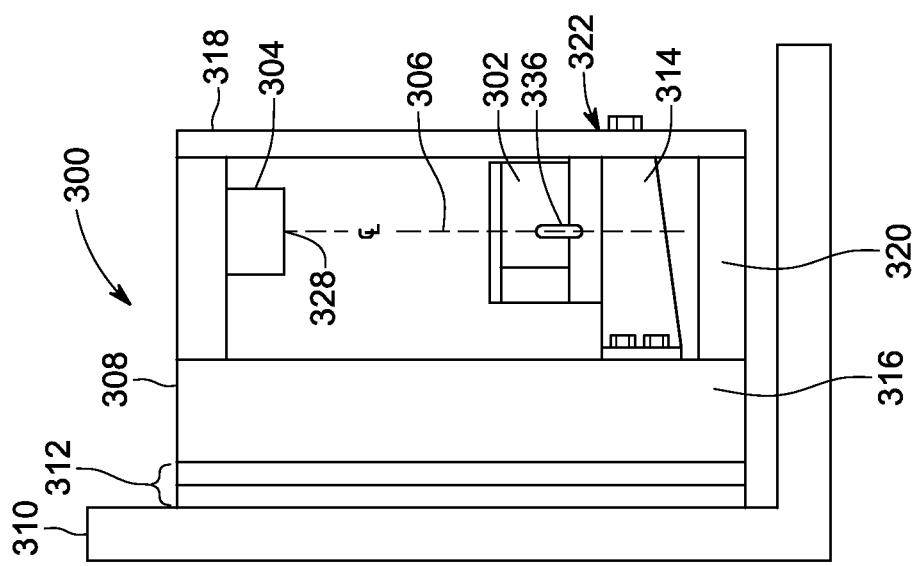
FIG. 3B
FIG. 3A

PACKAGING DESIGN FOR CT DETECTOR

BACKGROUND

This disclosure relates generally to diagnostic imaging and, more particularly, to an improved packaging design for a computed tomography (CT) detector assembly.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

The detector array (or assembly) and the x-ray tube are structurally mounted to the gantry. Generally, several issues can impact performance of the detector array. For instance, recent detector array designs include 3000 or more ASIC's that run at the same frequency, and can therefore cause electromagnetic interference (EMI). Also, detector assemblies include photodiodes that are light sensitive, which can lead to problems if there is external light exposure. Additionally, detector assemblies are often replaced in the field due to exposure to liquids that may include medical fluids, x-ray tube oil spills, and the like. The detectors are also subject to electrical problems if a ground loop is formed.

To mitigate such problems, detectors are designed to deal with each issue individually. For instance, multiple individual seals may be provided for detectors to reduce fluid contamination. However, overall the detector assembly is subject to EMI interference, light pollution, fluid contamination, and the like.

Therefore, it would be desirable to have a method and apparatus to collectively mitigate these issues.

BRIEF DESCRIPTION

Embodiments are directed toward an improved packaging design for a computed tomography (CT) detector assembly.

According to one aspect, a CT system includes a gantry having an opening for receiving an object to be scanned, an x-ray tube attached to the gantry, and a detector assembly. The detector assembly is positioned to receive x-rays that pass through the object and includes a light-sealed enclosure formed by at least first and second rails, a back support, and a light seal structure, and a plurality of liquid-cooled modules positioned in the enclosure. Each module includes a digital cable that passes from inside the enclosure, and each module is configured to convert the x-rays to a digital signal and output the signal via a digital cable.

According to another aspect, a method of assembling a CT system includes coupling a rotatable base to a gantry, the gantry having an opening for receiving an object to be scanned; attaching an x-ray tube to the gantry, forming a light-sealed enclosure by at least two rails, a back support, and a light seal structure, forming a detector assembly by positioning a plurality of liquid-cooled modules in the enclosure, wherein each module includes a digital cable that passes from inside the enclosure, and each module is configured to convert the x-rays to a digital signal and output the signal via a digital cable, and attaching the detector assembly to the gantry such that it is positioned to receive x-rays that pass through the object.

According to yet another aspect, a detector assembly for a CT imaging system includes a light-sealed enclosure formed by at least first and second rails, a back support, and a light seal structure, and a plurality of liquid-cooled modules positioned in the enclosure, each module comprising a digital cable that passes from inside the enclosure, and each module is configured to convert the x-rays to a digital signal and output the signal via a digital cable.

Various other features and advantages will be made apparent from the following detailed description and the drawings.

BRIEF DESCRIPTION OF THE DRAWINGS

FIGS. 3A and 3B are side and plan views of a detector assembly in a gantry, according to an example.

DETAILED DESCRIPTION

The operating environment of disclosed embodiments is described with respect to a sixty-four-slice computed tomography (CT) system. However, it will be appreciated by those skilled in the art that embodiments are equally applicable for use with other multi-slice configurations. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
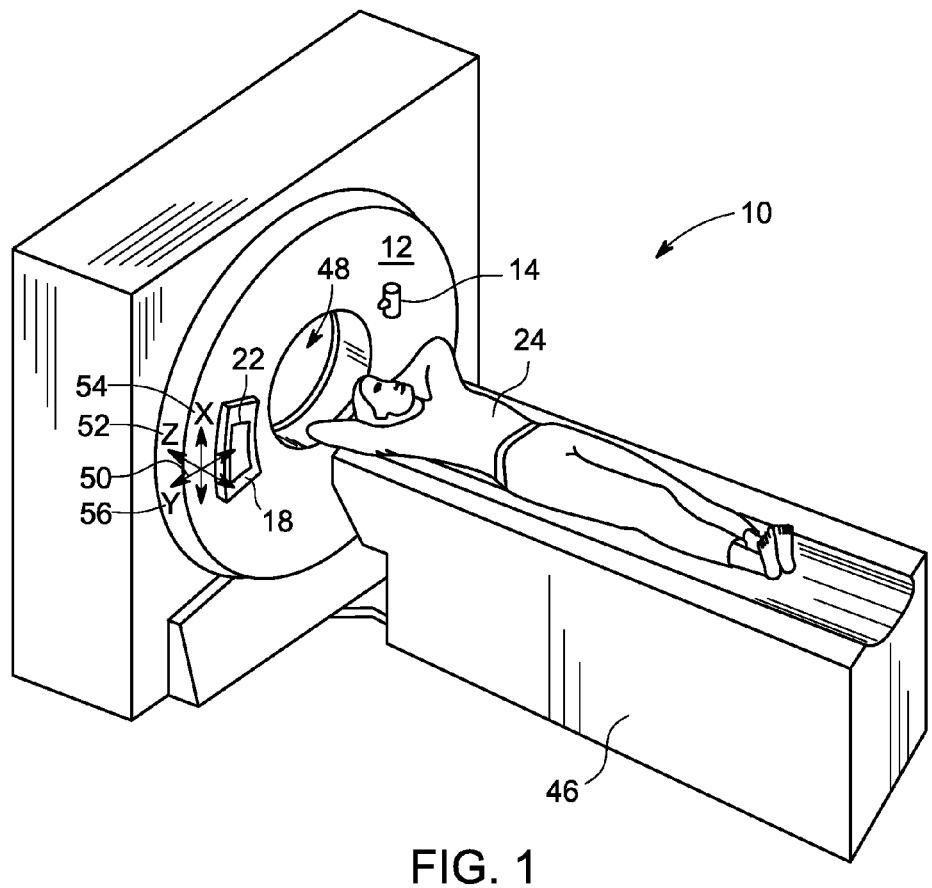
FIG. 1 is a pictorial view of a CT imaging system that incorporates disclosed embodiments.
Figure 2:
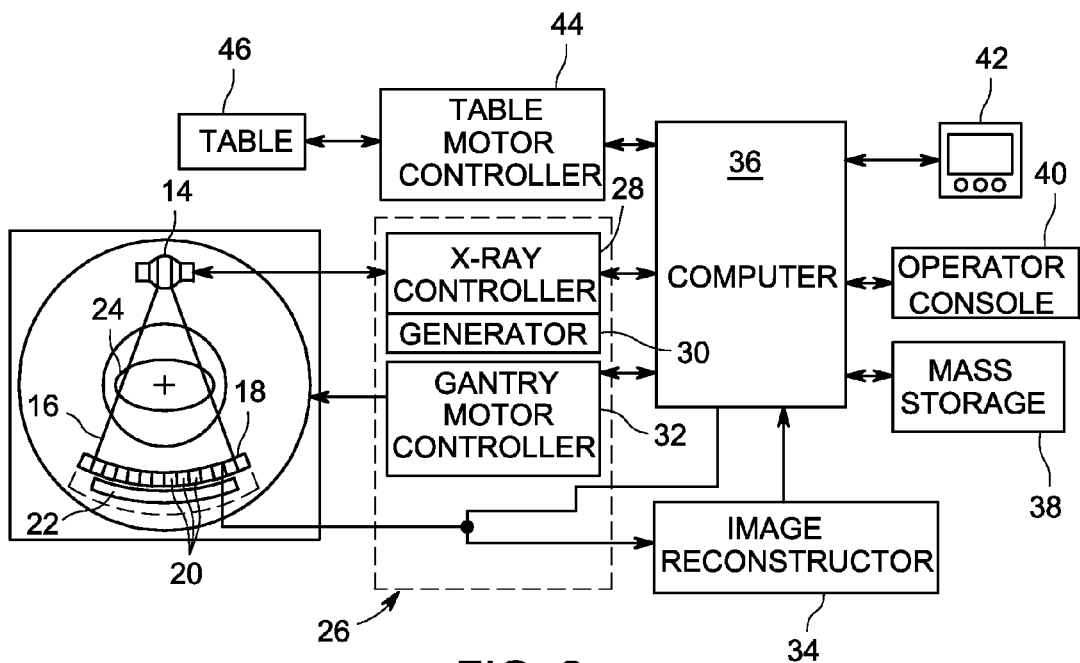
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray source 14 to detector assembly 18.

X-ray source 14, in accordance with present embodiments, is configured to emit x-rays or x-ray beam 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Referring to FIGS. 3A and 3B, side and plan views of a gantry are shown, according to embodiments, which may be incorporated into system 10 of FIGS. 1 and 2. Gantry 300 includes an arc-shaped or arcuate structure or detector assembly 302 and x-ray tube 304 that are coupled or mounted axially with respect to one another such that a centerline 306 of x-ray tube 304 corresponds with a center of detector assembly 302. Gantry 300 includes a rotatable base 308 positioned on or coupled to a stationary base 310, and having a bearing 312 mounted therebetween. Detector assembly 302 includes a plurality of detectors, as will be shown, which are positioned to receive x-rays that are generated by x-ray tube 304 and pass through an object, such as object 24 of FIG. 1. The detectors are positioned at approximately the same distance from a focal spot 328 of x-ray source 304. A support frame 314 is attached to rotatable base 308 at a first axial location 316. A support structure 318 such as a face plate is attached to rotatable base 308 via an axial extension support or drum 320 which, as one example, is a generally cylindrical shaped support structure and positioned radially external to support frame 314. Support frame 314 is thereby supported by support structure 318 at a second axial location 322. As such, detector assembly 302 is straddle mounted and supported on both axial locations 316, 322.

Detector assembly 302 extends along a generally circumferential direction and includes a surface 326 that is approximately radially equidistant from focal spot 328 of x-ray tube 304. X-ray tube 304 is positioned to generate x-rays toward detectors (not shown) mounted on surface 326, and x-ray tube 304 is attached to axial extension support 320. Support frame 314 is attached to rotatable base 308 at first axial location 316 and second axial location 322. Support frame 314 is also attached to rotatable base 316 at a first circumferential end 330 of arcuate structure 302. A second support frame 332 is attached to rotatable based 308 at a second circumferential end 334 of arcuate structure 302. According to one example, a locating pin 336 provides positioning location or restraint for detector assembly 302 with respect to support frame 314. Slots or holes may be positioned in each component 302, 314 such that accurate axial positioning is achieved. As such, detector assembly 302 may be positioned axially in a very accurate fashion with respect to x-ray tube 304 and particularly with respect to focal spot 328.

Detector assembly 302 is shown having a first mounting face 338 and a second mounting face 340, supported by corresponding support frames 314, 332. However, it is contemplated that alternate support frames (not shown) may also be implemented, such that a first surface 342 and a second surface 344 are used to support detector assembly 302.

Figure 4:
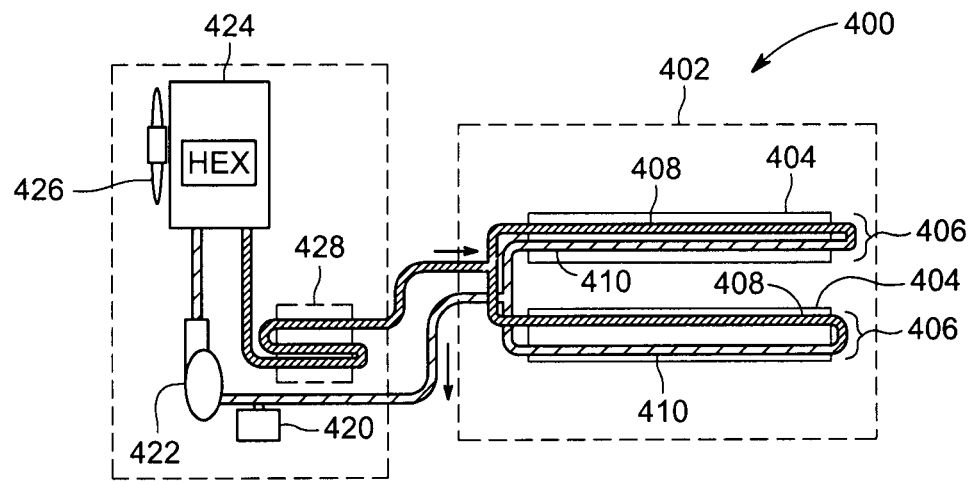
FIG. 4 is a schematic diagram of an exemplary cooling system that may be utilized to provide cooling for a detector.

FIG. 4 is a schematic diagram of an exemplary cooling system 400 that may be utilized to provide cooling for a detector illustrated, such as detector assembly 18. Cooling system 400 is in thermal communication with a plurality of detector rails 404 of a detector assembly 402, such as detector assembly 18 of FIGS. 1 and 2. In various embodiments, cooling channels 406 include a cool channel 408 and a hot channel 410. In one embodiment, cooling channels 406 may extend through detector rails 404. In one example, a cold plate (not shown) may be coupled to detector rails 404 and cooling channels 406 may extend through the cold plate. In another example, cooling channels 406 may be configured to extend both through detector rails 404 and the cold plate. The cooling channels 406 have cooling fluid flowing therethrough, which may be any suitable cooling fluid (e.g. liquid or gas).

In various embodiments, cooling system 400 includes an accumulator 420 and a pump 422 that are positioned downstream from the cooling channels 406. In operation, accumulator 420 receives cooling fluid from the cooling channels 406. The amount of cooling fluid received in accumulator 420 may depend on a pressure of the cooling fluid within cooling system 400. Pump 422 is positioned downstream of accumulator 420 to control a flow of the cooling fluid through cooling system 400. Pump 422 may be a single speed pump or a variable speed pump.

In operation, pump 422 discharges the cooling fluid downstream to a heat exchanger 424. Heat exchanger 424 may be any suitable heat exchanger, for example, an air-to-liquid heat exchanger or a liquid-to-liquid heat exchanger. In the illustrated embodiment, heat exchanger 424 is an air-to-liquid heat exchanger having a fan 426. The cooling fluid flows from heat exchanger 424 downstream to an inline heater 428. Inline heater 428 may be an electric heater, a gas heater, or any other suitable heater. Inline heater 428 discharges the cooling fluid downstream to the cooling channels 406.

During operation, cooling channels 406 receive the cooling fluid from inline heater 428. The cooling fluid is provided at a predetermined temperature that is configured to maintain a temperature of detector rails 404. More specifically, the cooling fluid in cool channels 408 cools detector rails 404 by receiving heat from detector rails 404 through at least one of thermal conduction or convection. The heated cooling fluid then flows through hot channels 410 downstream to accumulator 420. Accumulator 420 stores a portion of the cooling fluid based on a pressure within cooling system 400. For example, when cooling system 400 is operating at a higher pressure, accumulator 420 may store more cooling fluid than when the cooling system 400 is operating at a lower pressure. Accumulator 420 stores the cooling fluid to maintain a substantially constant operating pressure of cooling system 400. Accumulator 420 accounts for expansion of the cooling fluid at high pressures and may be utilized to pressurize pump 422, thereby, preventing cavitation within pump 422.

Pump 422 receives cooling fluid from accumulator 420. Pump 422 may be a variable speed pump that is controlled to adjust an amount of cooling fluid discharged to heat exchanger 424. By controlling a speed of pump 422, a temperature of the cooling fluid may be controlled. For example, increasing a speed of pump 422 increases the liquid flow rate as the cooling fluid travels through heat exchanger 424, which increases the cooling rate. Conversely, decreasing a speed of pump 422 decreases the liquid flow rate as the cooling fluid flows through heat exchanger 424, which decreases the cooling rate. In one embodiment, pump 422 discharges the cooling fluid to heat exchanger 424 at a flowrate that is configured to achieve the predetermined temperature of the cooling fluid.

In the illustrated embodiment, heat exchanger 424 receives the cooling fluid from pump 422. Heat exchanger 424 reduces the temperature of the cooling fluid to a temperature that is below the predetermined temperature. Fan 426 of heat exchanger 424 may be controlled to adjust the temperature of the cooling fluid. For example, fan 426 may be operated at a higher speed to reduce the temperature of the cooling fluid. Conversely, fan 426 may be operated at a lower speed to increase the temperature of the cooling fluid. A speed of fan 426 is controlled to achieve cooling of the cooling fluid to below the predetermined temperature.

The cooling fluid is discharged from heat exchanger 424 downstream to inline heater 428. Inline heater 428 increases the temperature of the cooling fluid from below the predetermined temperature to the predetermined temperature. In operation, inline heater 428 is capable of fine tuning the temperature of the cooling fluid, whereas, heat exchanger 424 may not be capable of providing regulation and control of temperatures. Accordingly, heat exchanger 424 is utilized to reduce the temperature of the cooling fluid to below the predetermined temperature. Inline heater 428 then fine tunes the temperature of the cooling fluid to achieve the predetermined temperature. The power supplied to inline heater 428 may be controlled to adjust the temperature of the cooling fluid. By adjusting the power supplied to inline heater 428, the heat produced by inline heater 428 is adjusted. For example, inline heater 428 may be operated at a higher power to increase the temperature of the cooling fluid. Conversely, inline heater 428 may be operated at a lower power to reduce the temperature of the cooling fluid. Inline heater 428 discharges the cooling fluid into the cool channels 406 at the predetermined temperature to maintain a temperature of detector rails 404.

Accordingly, in various embodiments, cooling system 400 is utilized to maintain a temperature of detector rails 404 at a steady-state temperature. Moreover, cooling system 400 facilitates reducing or preventing changes in the temperature of detector rails 404. Cooling system 400 may adjust several parameters to control the temperature of the cooling fluid. For example, any one of a speed of pump 422, a speed of fan 426, or a power of inline heater 428 may be adjusted to achieve the predetermined temperature of the cooling fluid.

Figure 5:
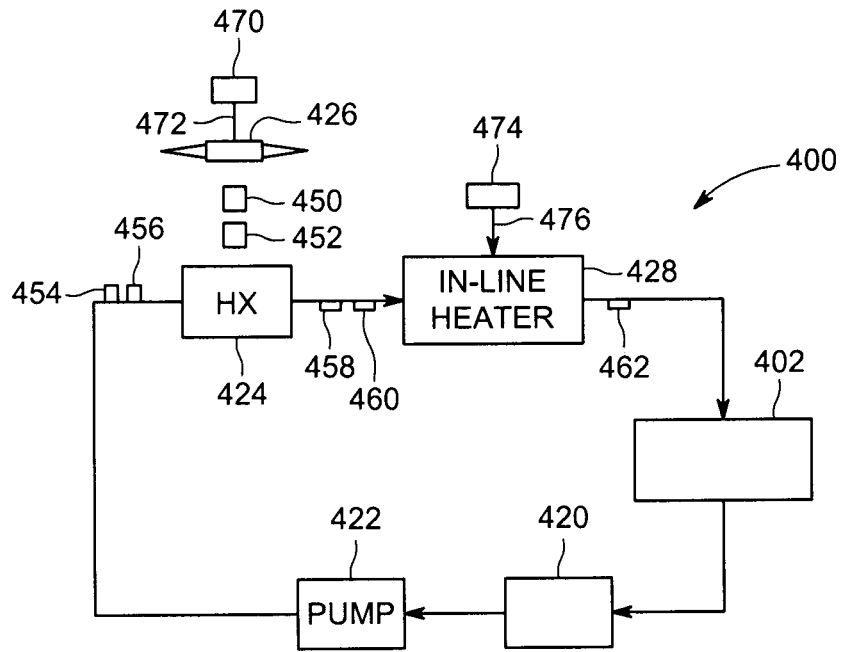
FIG. 5 illustrates a block diagram of the cooling system shown in FIG. 4.

FIG. 5 illustrates a detailed block diagram of cooling system 400 shown in FIG. 4. As described above, cooling system 400 includes accumulator 420, pump 422, heat exchanger 424, fan 426, and inline heater 428. Cooling system 400 also includes a plurality of temperature sensors that are disposed at various positions in cooling system 400. In various embodiments, the cooling system includes a first air temperature sensor 450 and a second air temperature sensor 452. In the exemplary embodiment, first and second air temperature sensors 450 and 452 are disposed proximate to fan 426 and are configured to output an electrical signal that indicates a temperature of the air entering heat exchanger 424, i.e. the ambient air temperature. In various embodiments, temperature sensors 450 and 452 therefore are redundant temperature sensors which each indicate the ambient air temperature.

Cooling system 400 also includes a third temperature sensor 454 and a fourth temperature sensor 456. In the exemplary embodiment, third and fourth temperature sensors 454 and 456 are disposed proximate to an inlet of heat exchanger 424 and are configured to output an electrical signal that indicates a temperature of the cooling fluid entering heat exchanger 424. In various embodiments, temperature sensors 454 and 456 therefore are redundant temperature sensors which each indicate the temperature of the cooling fluid entering heat exchanger 424.

Cooling system 400 also includes a fifth temperature sensor 458 and a sixth temperature sensor 460. In the exemplary embodiment, fifth and sixth temperature sensors 458 and 460 are disposed proximate to an outlet of heat exchanger 424 and are configured to output an electrical signal that indicates a temperature of the cooling fluid being discharged from the heat exchanger 424 and thus the temperature of the cooling fluid entering inline heater 428. In various embodiments, temperature sensors 458 and 460 therefore are redundant temperature sensors which each indicate the temperature of the cooling fluid being discharged from the heat exchanger 424.

Cooling system 400 also includes a seventh temperature sensor 462. In the exemplary embodiment, seventh temperature sensor 462 is disposed proximate to an outlet of inline heater 428 and is configured to output an electrical signal that indicates a temperature of the cooling fluid being discharged from inline heater 428. In various embodiments, cooling system 400 may also include an eighth temperature sensor (not shown) that also indicates a temperature of the cooling fluid being discharged from the inline heater 428. It should be realized that the temperature sensors shown in FIG. 5 are exemplary, and that cooling system 400 may include additional temperature sensors not shown in FIG. 5. For example, cooling system 400 may include additional temperature sensors that are installed in other positions on cooling system 400.

Cooling system 400 includes a fan speed controller 470. In operation, fan speed controller 470 is configured to control the operation of fan 426. More specifically, fan speed controller 470 is configured to transmit a signal 472 to fan 426 that either increases, decreases, or maintains the operational speed of fan 426. Cooling system 400 also includes a heater controller 474. In operation, heater controller 474 is configured to control the operation of inline heater 428. More specifically, heater controller 474 is configured to transmit a signal 476 to inline heater 428 that either increases, decreases, or maintains the operational temperature of the fluid being discharged from inline heater 428. As such, temperature sensors may provide input information for cooling control and heater control via fan 426 and inline heater 428, as examples, to properly maintain stable temperature during system operation.

Figure 6:
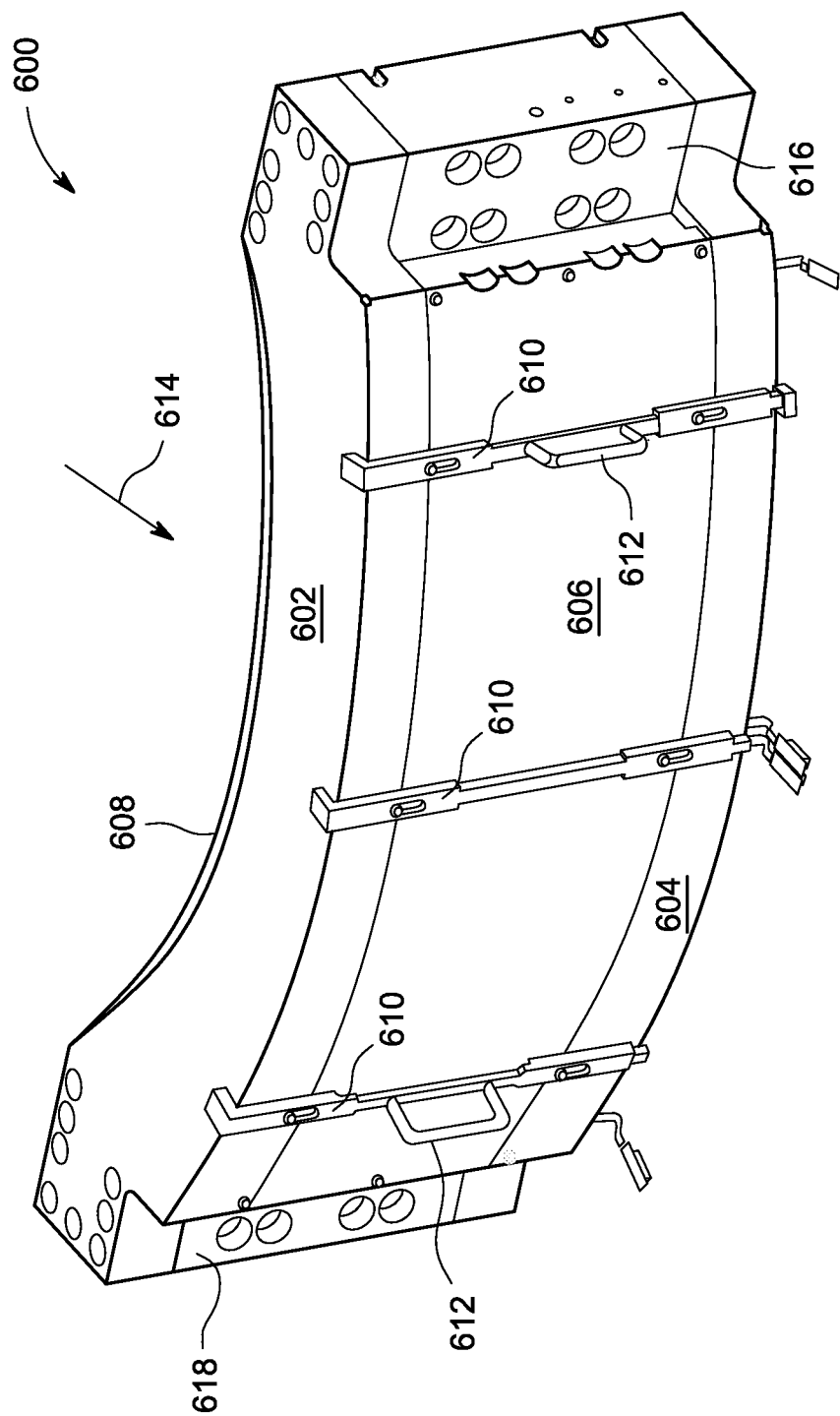
FIG. 6 illustrates a perspective view of a detector assembly according to one example.

FIG. 6 illustrates a detector assembly 600, which corresponds to detector assembly 18 of FIGS. 1 and 2, and detector assembly 302 of FIGS. 3A and 3B. Detector assembly 302 includes a first rail 602 and a second rail 604, and a back support 606 that is attached to rails 602, 604. A light seal structure 608 is positioned on the inner arc of detector assembly 600, providing a modular design that may be transported and installed, while providing protective surfaces for the detectors contained inside. Handling structures 610 are attached to assembly 600 for ease of handling and transportation of assembly 600. In the illustrated example, handling structures 610 include handles 612, to additionally facilitate handling of assembly 600. An enclosure is thereby formed using rails 602, 604, back support 606, and light seal 608, in which liquid-cooled modules are positioned, thereby providing EMI protection, liquid protection, and other benefits as will be further described.

Figure 7:
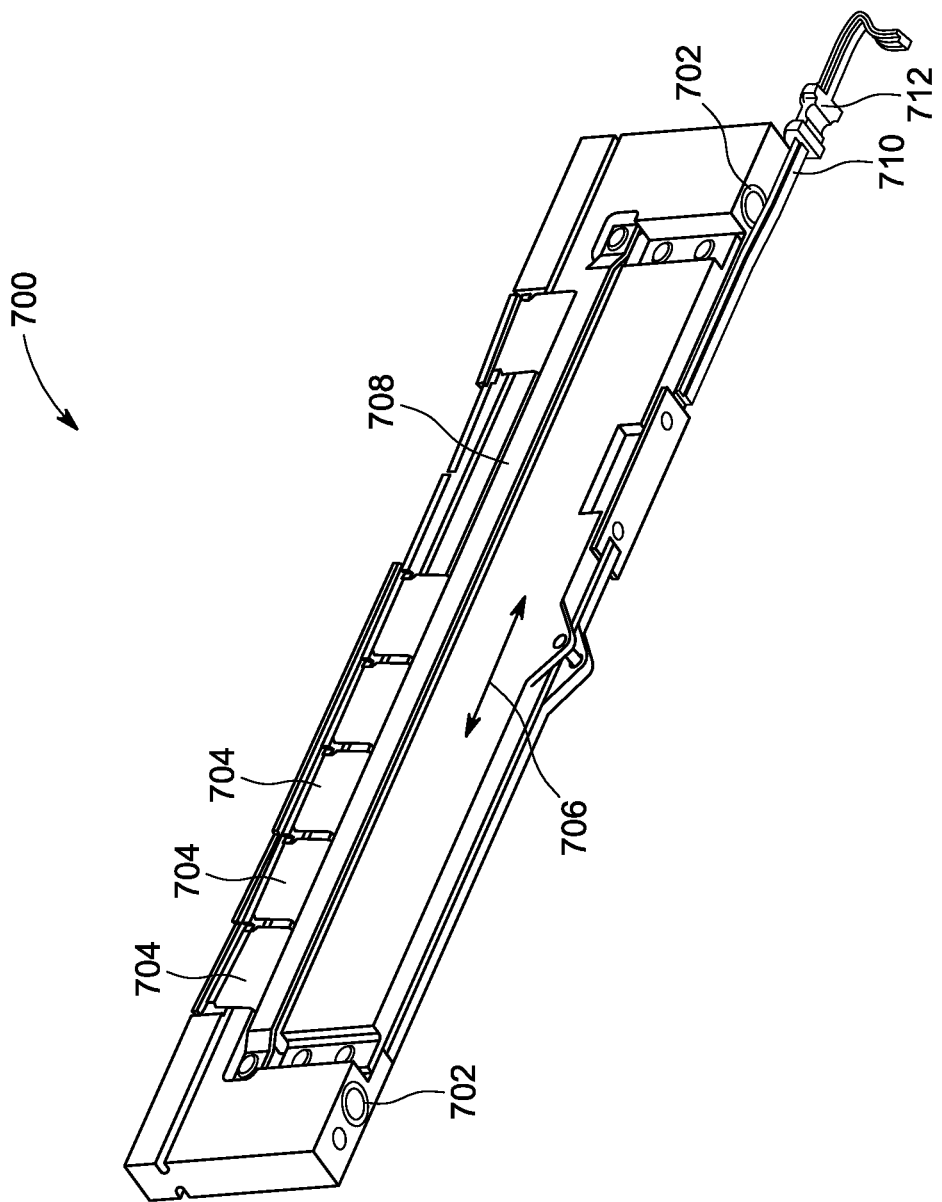
FIG. 7 illustrates a perspective view of a detector module.

FIG. 7 illustrates a detector module 700 having mounting holes 702, analog flex cables 704 (two of which are not shown, in the illustrated example) that pass to ASICs (not shown, underneath cooling structure 708. Detector module 700 extends in a z-direction 706, which corresponds with z-direction 52 of FIG. 1. As is commonly known, each module 700 includes scintillators, photodiodes (back lit in the illustrated example, in which readout of the photodiodes is on the back side of the photodiode), and the like. The ASICs convert analog signals from the photodiodes to digital signals, and additional processing and signal conditioning occurs in additional electronics (not shown). A digital signal is output via a digital cable 710.

Figure 8:
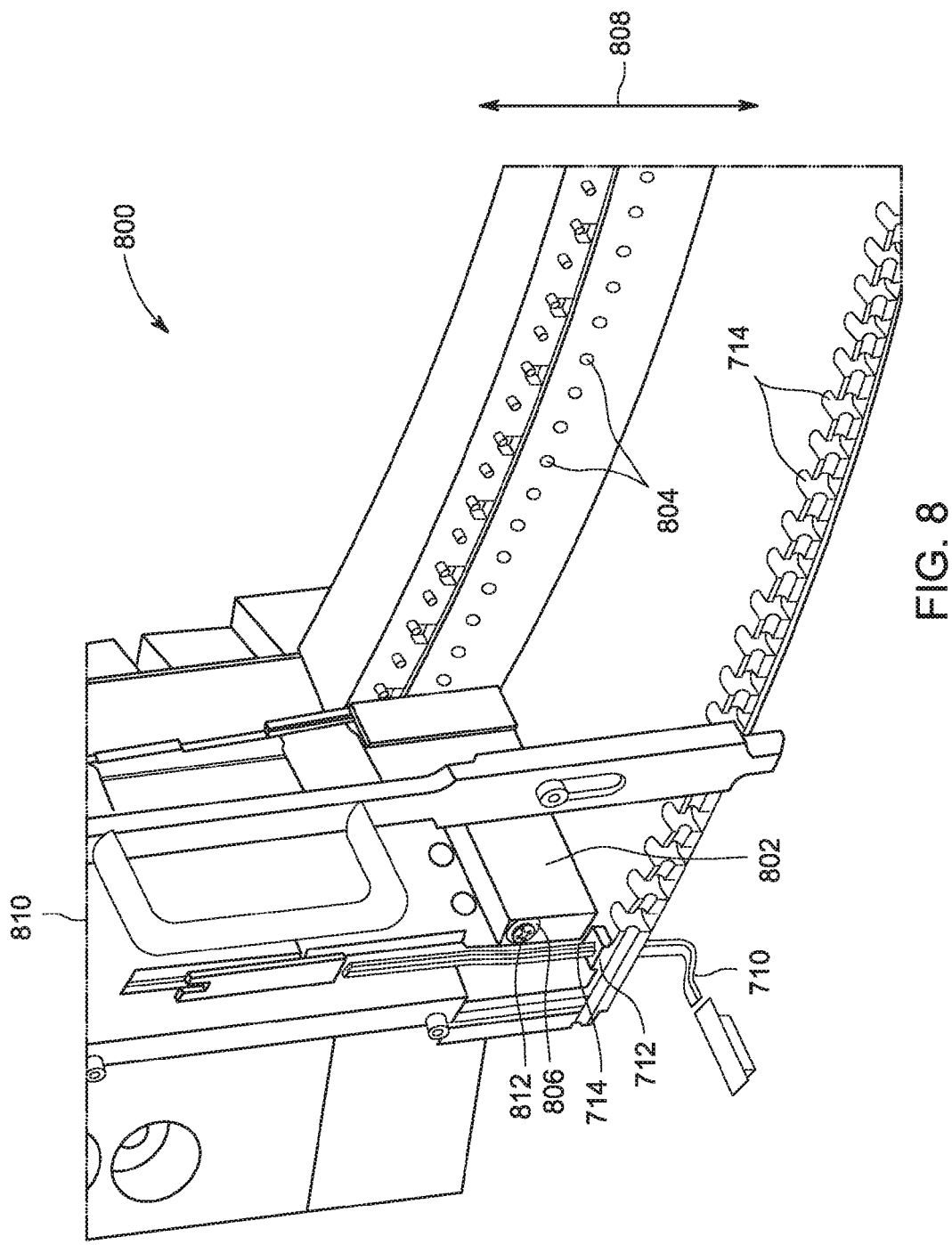
FIG. 8 illustrates a perspective view of one detector module installed within the detector assembly of FIG. 6, without a cover.

FIG. 8 illustrates an assembly 800, in which a module 802 (corresponding to module 700 of FIG. 7), is positioned and mounted within assembly 800. Assembly 800 includes an array of modules, similar to 802, which are mounted in the illustrated example into receiving holes 804, which correspond to mounting holes, such as a mounting hole 806 (corresponding also to mounting hole 702 of FIG. 7). Receiving holes 804 also are included in assembly 800 at a location that is at the opposite end of each module 802, although not illustrated therein. That is, each module extends along a width 808 of assembly 800, and mounting hole 806 is used at a first end of module 802, and a corresponding mounting hole at the other end of module 802 and not shown, is used to mount module 802 to the assembly 800 at the other end of module 802. For illustration purposes, assembly 800 shows a handling structure 810, although it is to be understood that the mounting structure is not positionable as shown until after all modules 802 are installed, and a cover (such as back support 606 of FIG. 6) is installed. In one example, a fastener 12 such as a screw is passed through mounting hole 806 and into a corresponding receiving hole 804 that, in one example, is threaded.

Figure 9:
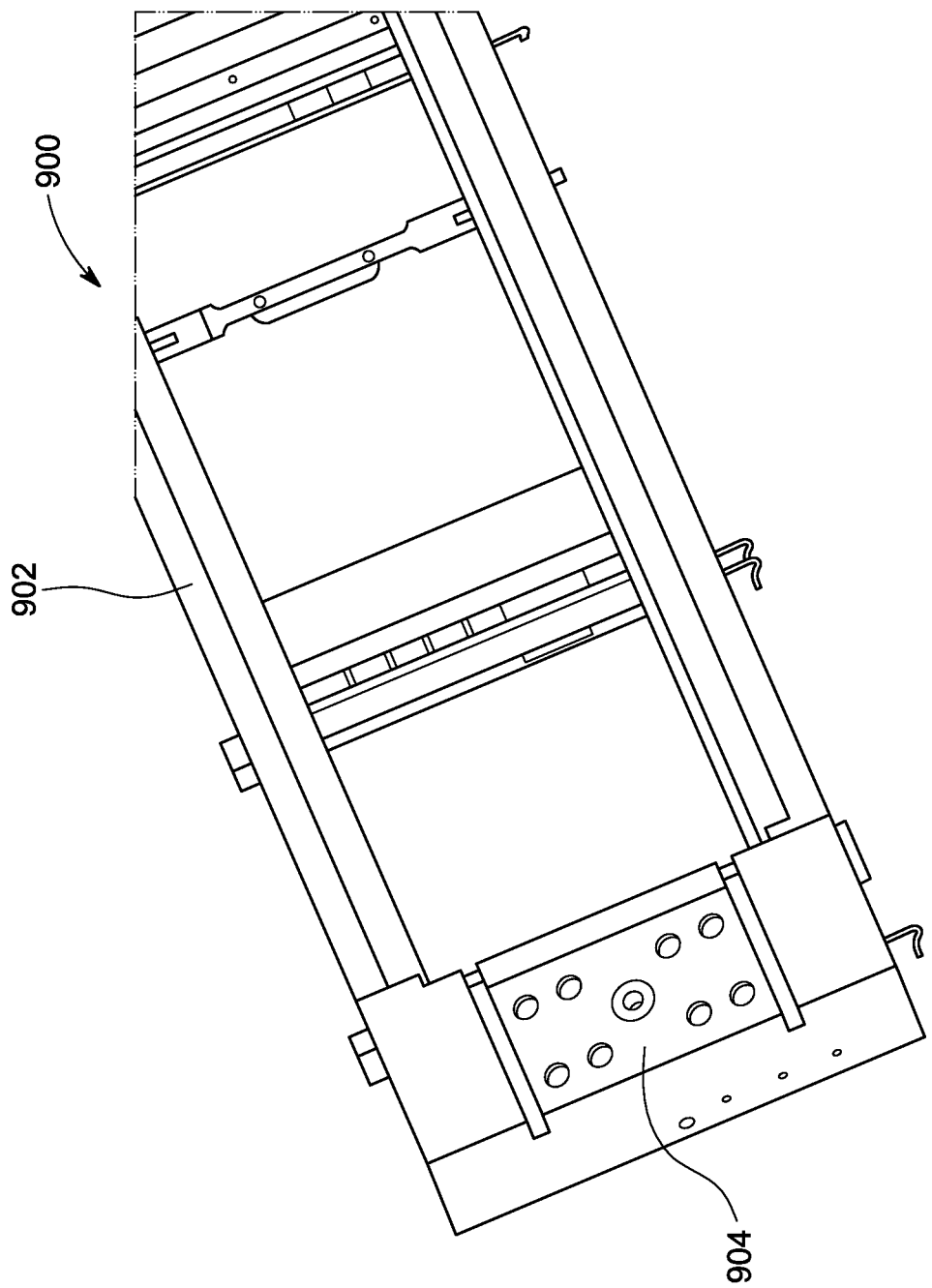
FIG. 9 illustrates a bottom view of the detector assembly of FIG. 6, without a window, and as viewed approximately from the x-ray source.

FIG. 9 illustrates a bottom view 900 of the detector assembly of FIG. 6, without a window, and as viewed approximately from the x-ray source. That is, bottom view 900 is a view of the inner arc of the detector assembly, as would be viewed approximately along a ray 614 of FIG. 6. Bottom view 900 shows assembly 902, but without a window or light seal, such as light seal 608 of FIG. 6. Typically, the window or light seal is fabricated of a relatively low density or low x-ray attenuating material, such that x-rays that pass from an x-ray tube are as little attenuated as possible, while meeting any structural and light sealing requirements. That is, typically the light seal is attached to the assembly 902 to prevent light from interfering with light generated within the scintillators of the detector modules. The light seal also is of sufficient mechanical integrity to withstand the heavy g-loading experienced by the detector assembly during operation. In one example, the light seal is fabricated of carbon fiber and attached to assembly 902 using electrical tape. Back support 606 (of FIG. 6) is sealed using a single piece metal cover and an electrically conductive elastomer, in one example, that can also double as a fluid seal.

Assembly 902 also includes a mounting or interface plate 904 that provides both electrical and thermal isolation between the assembly 902 and the gantry structure to which assembly is mounted. Interface plate 904 may include a ceramic such as alumina, or other electrically insulating material, that likewise provides relatively low thermal conductivity. In such fashion, the detector assembly 902 is mounted to the gantry in such a fashion that electrical activity or noise generated in and around the gantry do not interfere with the operation of the electronics in each module (and in the other electrical components) within detector assembly 902. Further, it is contemplated that, as stated above with respect to FIGS. 3A and 3B, detector assembly 302 may be mounted as shown and using mounting faces 338, 340 (which correspond to faces 616, 618 of FIG. 6). Or, detector assembly 302 may be mounted using surfaces 342, 344 in an alternate arrangement (not shown). Thus, in either arrangement, it is contemplated that interface plate 904 is positioned at the interface between detector assembly 302, and its corresponding mount faces of FIGS. 3A and 3B.

Thus, the illustrated detector assembly 600 provides an integrated packaging design of a CT detector that provides an EMI shield, a light seal, a fluid seal, and a Faraday cage. Internally to the assembly 600, other electronics such as a digital board are shielded locally to the modules therein. The modules are sealed by using the detector rails 602, 604 that form assembly 600, as well as light seal 608 and back support 606. In such fashion, assembly 600 may be fabricated in a clean and controlled environment, then sealed while still in the manufacturing environment, then shipped to sites for installation or swapping with other units that may need repair or replacement.

In one example, referring back to FIGS. 7 and 8, digital cable 710 is captured by an electrically conductive grommet 712, which is itself positioned in one of the several grommet mount slots or cutouts 714 that correspond to each module mounted within assembly 800. By integrating the cable grommet 712 into the rail cutout 714 and cover (not shown in FIG. 7), a complete Faraday cage is achieved around the detector. Additionally, the entire detector assembly is isolated thermally and electrically by incorporation of the interface plates, at each point where the detector assembly mounts to the gantry. In one example, an electrical drain wire (not shown) may be coupled from a cable within the detector assembly and tied to the grommet. The isolation plates themselves may be "tunable", in that a proper thickness is selected to provide the proper amount of thermal isolation and/or electrical isolation.

As such, EMI is suppressed for all the ASICs within the detector assembly, and the many FPGAs running at one frequency are thereby shielded from outside electrical interference, both from external RF noise, as well as noise that may be conducted within the mounting structure itself. Each detector module is light-sealed by fabricating an enclosure that may be sealed from external light, avoiding light interference in the photodiodes during detector operation. One enabling feature of the detector design, that allows for the operation in an enclosure, is the liquid cooling aspects described above. As summarized with respect to FIGS. 4 and 5, liquid cooling enables heat transfer out of the enclosure using lines that move heat transfer liquid (such as water or glycol) to pass in and out of the detector assembly. In such fashion, the requirement for convection cooling over the surface of the modules (and using air) is effectively removed, and heat is transferred via the liquid coolant. Further, by enclosing the electronics in a liquid tight enclosure, damage from external fluids is mitigated. In addition, the overall detector assembly may be floated electrically (by use of the interface plates), and grounded through the cables, preventing ground loops due to chassis and voltage variations that may arise in the assembly. And, the use of an electrically conductive grommet, EMI paths are eliminated.

Thus, global shielding of the detector is accomplished to reduce or eliminate EMI interference. Leak points are reduced or eliminated, and fluid damage from external fluid sources are eliminated. Field replacement of the detector assembly is thus facilitated in that a single unit is handled, transported, and installed, without need for costly and time-consuming module replacement or repair in the field. Thermal isolation from the isolator plates also reduces the heat load on the detector assembly, reducing the size and cost of the heat exchanger for the system.

Figure 10:
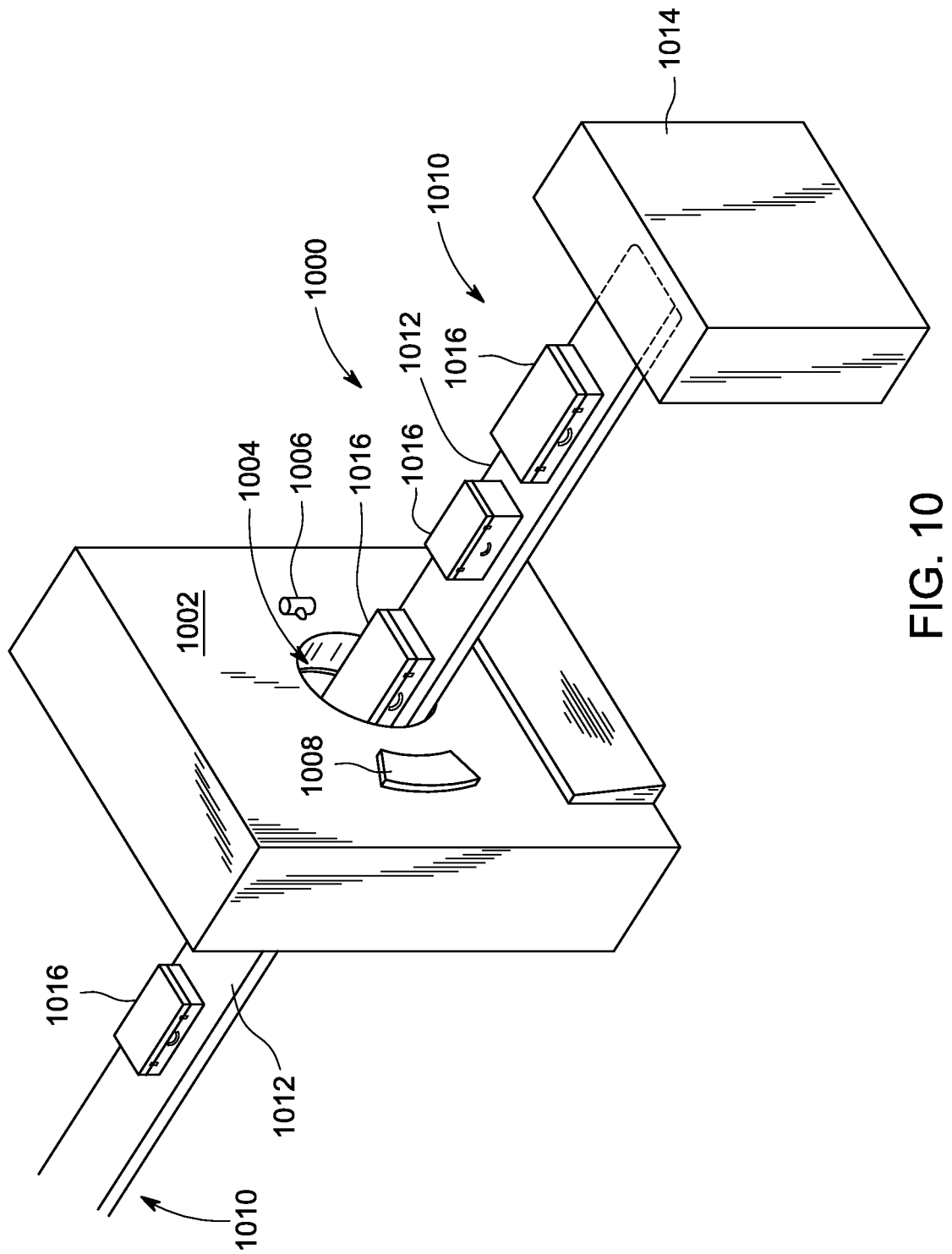
FIG. 10 is a pictorial view of a CT system for use with a non-invasive package inspection system according to an embodiment.

Referring now to FIG. 10, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, a CT system includes a gantry having an opening for receiving an object to be scanned, an x-ray tube attached to the gantry, and a detector assembly. The detector assembly is positioned to receive x-rays that pass through the object and includes a light-sealed enclosure formed by at least first and second rails, a back support, and a light seal structure, and a plurality of liquid-cooled modules positioned in the enclosure. Each module includes a digital cable that passes from inside the enclosure, and each module is configured to convert the x-rays to a digital signal and output the signal via a digital cable.

According to another embodiment, a method of assembling a CT system includes coupling a rotatable base to a gantry, the gantry having an opening for receiving an object to be scanned; attaching an x-ray tube to the gantry, forming a light-sealed enclosure by at least two rails, a back support, and a light seal structure, forming a detector assembly by positioning a plurality of liquid-cooled modules in the enclosure, wherein each module includes a digital cable that passes from inside the enclosure, and each module is configured to convert the x-rays to a digital signal and output the signal via a digital cable, and attaching the detector assembly to the gantry such that it is positioned to receive x-rays that pass through the object.

According to yet another embodiment, a detector assembly for a CT imaging system includes a light-sealed enclosure formed by at least first and second rails, a back support, and a light seal structure, and a plurality of liquid-cooled modules positioned in the enclosure, each module comprising a digital cable that passes from inside the enclosure, and each module is configured to convert the x-rays to a digital signal and output the signal via a digital cable.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed subject matter has been described in detail in connection with only a limited number of embodiments, it should be readily understood that the disclosed subject matter is not limited to such disclosed embodiments. Rather, that disclosed can be modified to incorporate any number of variations, alterations, substitutions or equivalent arrangements not heretofore described, but which are commensurate with the spirit and scope of the disclosed subject matter. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A CT system comprising:
    a gantry having an opening for receiving an object to be scanned;
    an x-ray tube attached to the gantry; and
    a detector assembly positioned to receive x-rays that pass through the object, the detector assembly comprising:
        a light-sealed enclosure formed by at least first and second rails, a back support, and a light seal structure; and
        a plurality of liquid-cooled modules positioned in the enclosure, each module comprising a digital cable that passes from inside the enclosure, and each module is configured to convert the x-rays to a digital signal and output the signal via a digital cable, wherein one of the first and second rails includes grommet cutouts with grommets positioned in the grommet cutouts, and the respective digital cables pass through the grommet cutouts, and the grommets are electrically conductive.

2. The CT system of claim 1, wherein the detector assembly includes a plurality of receiving holes in the enclosure, each of which corresponds to a mounting hole within each module, such that the module is mounted within the enclosure via a fastener.

3. The CT system of claim 1, further comprising a handling structure attached to the detector assembly for ease of transportation and handling of the detector assembly.

4. The CT system of claim 3, wherein the handling structure further comprises a handle attached thereto.

5. The CT system of claim 1, further comprising an interface plate attached to the detector assembly, the interface plate positioned between the detector assembly and the gantry.

6. The CT system of claim 5, wherein the interface plate is alumina.

7. A method of assembling a CT system, comprising:
    coupling a rotatable base to a gantry, the gantry having an opening for receiving an object to be scanned;
    attaching an x-ray tube to the rotatable base;
    forming a light-sealed enclosure by at least two rails, a back support, and a light seal structure;
    forming a detector assembly by positioning a plurality of liquid-cooled modules in the enclosure, wherein each module includes a digital cable that passes from inside the enclosure, and each module is configured to convert the x-rays to a digital signal and output the signal via a digital cable, wherein one of the two rails includes grommet cutouts with grommets positioned in the grommet cutouts, and the respective digital cables pass through the grommet cutouts, and the grommets are electrically conductive; and
    attaching the detector assembly to the rotatable table such that it is positioned to receive x-rays that pass through the object.

8. The method of claim 7, wherein the enclosure includes a plurality of receiving holes, each of which corresponds to a mounting hole within each module, such that the module is mounted within the enclosure via a fastener.

9. The method of claim 7, further comprising attaching a handling structure to the detector assembly for ease of transportation and handling of the detector assembly.

10. The method of claim 9, wherein the handling structure further comprises a handle attached thereto.

11. The method of claim 7, further comprising attaching an interface plate to the detector assembly, the interface plate positioned between the detector assembly and the gantry.

12. A detector assembly for a CT imaging system, the assembly comprising:
    a light-sealed enclosure formed by at least first and second rails, a back support, and a light seal structure; and
    a plurality of liquid-cooled modules positioned in the enclosure, each module comprising a digital cable that passes from inside the enclosure, and each module is configured to convert the x-rays to a digital signal and output the signal via a digital cable, wherein one of the first and second rails includes grommet cutouts with grommets positioned in the grommet cutouts, and the respective digital cables pass through the grommet cutouts, and the grommets are electrically conductive.

13. The detector assembly of claim 12, wherein the detector assembly includes a plurality of receiving holes in the enclosure, each of which corresponds to a mounting hole within each module, such that the module is mounted within the enclosure via a fastener.

14. The detector assembly of claim 12, further comprising a handling structure attached to the detector assembly for ease of transportation and handling of the detector assembly.

15. The detector assembly of claim 14, wherein the handling structure further comprises a handle attached thereto.

16. The detector assembly of claim 12, further comprising an interface plate attached to the detector assembly, the interface plate positioned to attach the detector assembly to a gantry.

17. The detector assembly of claim 16, wherein the interface plate is alumina.

* * * * *